United States Patent

Meier et al.

Patent Number: 4,461,898
Date of Patent: Jul. 24, 1984

[54] PROCESS FOR THE PREPARATION OF NOVEL LIGHT STABILIZERS

[75] Inventors: Anton Meier, Magden; Eduard Troxler, Basel, both of Switzerland

[73] Assignee: Ciba-Geigy Corporation, Ardsley, N.Y.

[21] Appl. No.: 437,929

[22] Filed: Nov. 1, 1982

[30] Foreign Application Priority Data

Nov. 10, 1981 [CH] Switzerland ............ 7207/81

[51] Int. Cl.³ .................. C07D 401/12; C07D 401/06; C08K 5/34
[52] U.S. Cl. .................. 546/188; 546/222; 546/242; 524/102
[58] Field of Search .................. 546/188, 222, 242

[56] References Cited

U.S. PATENT DOCUMENTS

Re. 31,343  8/1983  Holt et al. .................. 546/188
4,021,432  5/1977  Holt et al. .................. 546/188

Primary Examiner—Robert T. Bond
Attorney, Agent, or Firm—Luther A. R. Hall

[57] ABSTRACT

Mixtures of esters of polyalkylpiperidine derivatives, of the formulae I and II

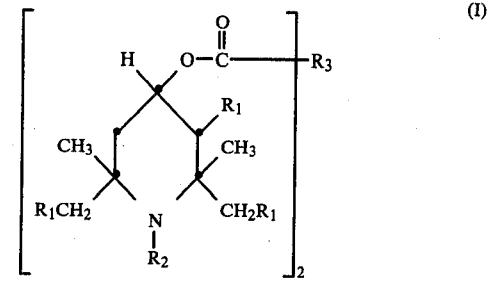

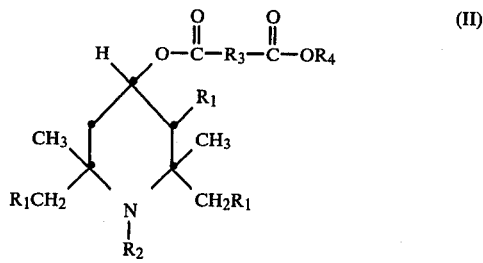

in which the proportions of I to II are 95 to 70% by weight and 5 to 30% by weight, are obtained by reacting about 2 mols of a piperidine of the formula III

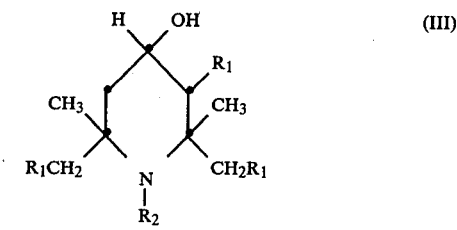

with 0.9 to 1.3 mols of a diester of the formula IV

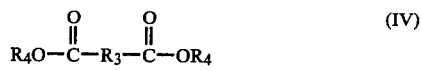

in the melt at between 100° and 145° C., in the presence of an alkali metal amide as a catalyst.

The mixtures of esters thus obtained are very suitable as light stabilizers for plastics.

5 Claims, No Drawings

PROCESS FOR THE PREPARATION OF NOVEL LIGHT STABILIZERS

The invention relates to a process for the preparation of novel mixtures of esters of polyalkylpiperidine derivatives.

Polyalkylpiperidine esters, such as bis-(1,2,2,6,6-pentamethyl-4-piperidyl) sebacate, are known from U.S. Pat. No. 4,021,432 as light stabilisers for plastics. For practical application, known stabilisers of this type have not proved satisfactory in all cases. In particular when using solid substances, if appropriate also in the form of solutions, there are disadvantages in practice and these give rise to problems, for example in the preparation of light-stable lacquers such as car lacquers. Thus, the known light stabilisers are not suitable for use in solvent poor lacquer systems (high solids).

The present invention relates to a process for the preparation of mixtures of esters of polyalkylpiperidine derivatives, of the formulae I and II

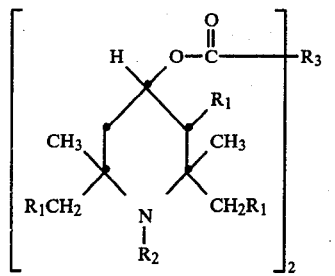

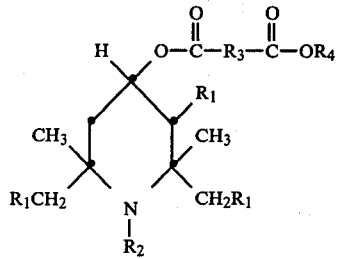

in which $R_1$ is hydrogen or methyl, $R_2$ is hydrogen, $C_{1-12}$ alkyl, $C_{3-8}$ alkenyl, $C_{7-11}$ aralkyl, cyanomethyl or $C_{2-4}$ acyl, $R_3$ is $C_{1-18}$ alkylene, $C_{2-18}$ oxaalkylene, $C_{2-18}$ thiaalkylene, $C_{2-18}$ azaalkylene or $C_{2-8}$ alkenylene, $R_4$ is $C_{1-4}$ alkyl and the proportions of the two esters vary between 95 to 70% by weight, preferably 90 to 75% by weight, of I and 5 to 30% by weight, preferably 10 to 25% by weight, of II, which comprises reacting about 2 mols of a piperidine of the formula III

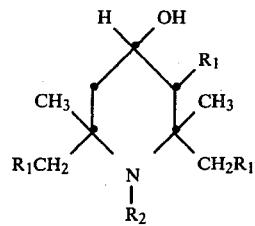

with 0.9 to 1.3 mols, preferably 1.1 to 1.25 mols, of a diester of the formula IV

in which $R_1$, $R_2$, $R_3$ and $R_4$ are as defined above, in the melt at between 100° and 145° C., preferably at 125° to 140° C., in the presence of an alkali metal amide, preferably lithium amide, as a catalyst.

After the reaction, the alcohol formed is distilled off, preferably in vacuo, in particular at a pressure of between 0.6 bar and 10 mbar and very particularly preferably at 15 to 25 mbar. The product is worked up by customary methods.

The starting materials are known. Should some of them be novel, however, they can be prepared analogously to those which are known.

$C_{1-12}$ Alkyl $R_2$ is especially straight-chain alkyl having, in particular, 1 to 4 C atoms, such as ethyl, n-propyl, n-butyl and, in particular, methyl.

$C_{3-8}$ Alkenyl $R_2$ is especially straight-chain alkenyl, in particular allyl.

$C_{7-11}$ Aralkyl $R_2$ is especially benzyl.

$C_{2-4}$ Acyl $R_2$ is especially alkanoyl or alkenoyl, such as propionyl, acryloyl and, in particular, acetyl.

$C_{1-18}$ Alkylene $R_3$ is branched or especially straight-chain alkylene, in particular alkylene having 1 to 10 C atoms, such as methylene, ethylene, trimethylene, tetramethylene, hexamethylene, decamethylene and, in particular, octamethylene.

$C_{2-18}$ Oxaalkylene $R_3$ is especially straight-chain oxaalkylene having, in particular 2 to 9 C atoms, such as 2-oxa-trimethylene or 3-oxa-pentamethylene.

$C_{2-18}$ Thiaalkylene $R_3$ is especially straight-chain thiaalkylene having, in particular, 2 to 9 C atoms, such as 2-thia-trimethylene or 3-thia-pentamethylene.

$C_{2-18}$ Azaalkylene $R_3$ is straight-chain or branched azaalkylene, especially azaalkylene branched at the aza group, having, in particular, 2 to 9 C atoms, such as 3-aza-pentamethylene, 3-aza-3-methyl-pentamethylene, 4-aza-heptamethylene of 4-aza-4-methyl-heptamethylene.

$C_{2-8}$ Alkenylene $R_3$ is especially straight-chain alkenylene, such as ethenylene or 2-buten-1,4-ylene.

$C_{1-4}$ Alkyl $R_4$ is, for example, ethyl, n-propyl, i-propyl, n-butyl, i-butyl or, in particular, methyl.

The process according to the invention is particularly suitable for the preparation of mixtures of esters of the formulae I and II in which $R_1$ is hydrogen, $R_2$ is $C_{1-4}$ alkyl or benzyl, $R_3$ is $C_{1-18}$ alkylene and $R_4$ is $C_{1-4}$ alkyl.

The process according to the invention is very particularly suitable for the preparation of mixtures of esters of the formulae I and II in which $R_1$ is hydrogen, $R_2$ is methyl or benzyl, $R_3$ is straight-chain $C_{2-10}$ alkylene and $R_4$ is $C_{1-14}$ alkyl.

The preferred process according to the invention is the process for the preparation of mixtures of esters of the formulae I and II in which $R_1$ is hydrogen, $R_2$ is methyl, $R_3$ is octamethylene and $R_4$ is methyl.

It has been shown that the mixtures of esters obtained by the process according to the invention are particularly good light stabilisers for plastics, which do not show the disadvantages mentioned above in respect of the polyalkylpiperidine esters described in U.S. Pat. No. 4,021,432, or show these disadvantages to a substantially smaller extent. They are very compatible with the substrate and can be incorporated therein without difficulties. They disperse rapidly and homogeneously in the substrate, the latter being effectively and durably protected against the harmful effect of light. The process according to the invention makes it possible to obtain the abovementioned mixtures of esters in the desired proportions and in quantitative yield.

The following examples illustrate the invention without limiting it.

EXAMPLE 1:

152.6 g (0.663 mol) of dimethyl sebacate and 189.5 g (1.106 mols) of 1,2,2,6,6-pentamethyl-4-hydroxy-piperidine are melted, under nitrogen, by warming to 95° C. At 95° C., 1 g of lithium amide is added. The mixture is then warmed to 125° to 130° C. and the reaction starts, methanol being distilled off. After about 30 ml of methanol have been distilled off, the mixture is cooled to 100° C. and a vacuum of 0.6 bar is applied. The mixture is then heated to 140° C. in vacuo, the vacuum decreasing to 20 to 25 mbar. After stirring for 2 to 3 hours at 140° C., the reaction has finished. To work up the product, the reaction mixture is cooled to 80° C., treated with 100 ml of a gasoline fraction (boiling range 80° to 110° C.), extracted with 50 ml of 15 to 20% by weight aqueous acetic acid and then re-extracted with 50 ml of water. After the aqueous phase has been separated off, the organic phase is dried azeotropically by heating the mixture to 110° C. and separating off the water via a separator. The organic phase is then clarified through a suction filter covered with a filter aid, and the gasoline is distilled off in vacuo at 110° C. Yield: 283.2 g (quantitative). The pale yellowish, oily liquid obtained is a mixture of about 80% of bis-(1,2,2,6,6-pentamethyl-4-piperidinyl) sebacate and about 20% of mono-(1,2,2,6,6-pentamethyl-4-piperidinyl) monomethyl sebacate.

EXAMPLE 2

The procedure is the same as in Example 1, but 139.9 g (0.609 mol) of dimethyl sebacate and 189.5 g (1.106 mols) of 1,2,2,6,6-pentamethyl-4-hydroxypiperidine are used. This yields 271 g of a pale yellowish, oily liquid consisting of 90% of bis-(1,2,2,6,6-pentamethyl-4-piperidinyl) sebacate and about 10% of mono-(1,2,2,6,6-pentamethyl-4-piperidinyl) monomethyl sebacate.

EXAMPLE 3

The procedure is the same as in Example 1, but 397.5 g (1.728 mols) of dimethyl sebacate and 473.8 g (2.765 mols) of 1,2,2,6,6-pentamethyl-4-hydroxypiperidine are used. 2.5 g of lithium amide are required as a catalyst. The extractions are carried out with 130 ml of 15 to 20% by weight aqueous acetic acid and with 120 ml of water. This yields 747.9 g of a pale yellowish, oily liquid consisting of 75% of bis-(1,2,2,6,6-pentamethyl-4-piperidinyl) sebacate and about 25% of mono-(1,2,2,6,6-pentamethyl-4-piperidinyl) monomethyl sebacate.

What is claimed is:

1. A process for the preparation of a mixture of esters of polyalkylpiperidine derivatives, of the formulae I and II

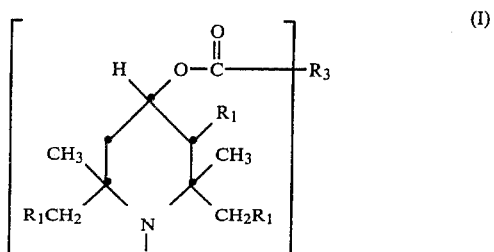

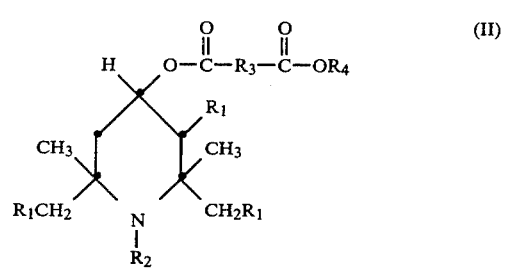

in which $R_1$ is hydrogen or methyl, $R_2$ is hydrogen, $C_{1-12}$ alkyl, $C_{3-8}$ alkenyl, $C_{7-11}$ aralkyl, cyanomethyl or $C_{2-4}$ acyl, $R_3$ is $C_{1-18}$ alkylene, $C_{2-18}$ oxaalkylene, $C_{2-18}$ thiaalkylene, $C_{2-18}$ azaalkylene or $C_{2-8}$ alkenylene, $R_4$ is $C_{1-4}$ alkyl and the proportions of the two esters vary between 95 to 70% by weight of I and 5 to 30% by weight of II, which comprises reacting about 2 mols of a piperidine of the formula III

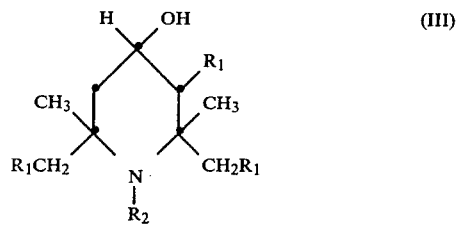

with 0.9 to 1.3 mols of a diester of the formula IV

in which $R_1$, $R_2$, $R_3$ and $R_4$ are as defined above, in the melt at between 100° and 145° C., in the presence of an alkali metal amide as a catalyst.

2. A process according to claim 1, wherein the alcohol formed during the reaction is distilled off in vacuo.

3. A process according to claim 1, wherein a mixture of esters with proportions of 90 to 75% by weight of ester I and 10 to 25% by weight of ester II is obtained when using about 2 mols of a piperidine of the formula III and 1.1 to 1.25 mols of a diester of the formula IV.

4. A process according to claim 1, wherein the reaction is carried out at a temperature between 125° and 140° C.

5. A process according to claim 1, wherein lithium amide is used as the catalyst.

* * * * *